(12) United States Patent
Stahmann et al.

(10) Patent No.: US 8,096,954 B2
(45) Date of Patent: Jan. 17, 2012

(54) ADAPTIVE SAMPLING OF HEART SOUNDS (75) Inventors: Jeffrey E. Stahmann, Ramsey, MN (US); Krzysztof Z. Siejko, Maple Grove, MN (US); Carlos Haro, St. Paul, MN (US); Abhilash Patangay, Little Canada, MN (US); Gerrard M. Carlson, Champlin, MN (US); Andres Belalcazar, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 776 days.

(21) Appl. No.: 11/564,637

(22) Filed: Nov. 29, 2006

(65) Prior Publication Data

US 2008/0125820 A1    May 29, 2008

(51) Int. Cl.
    *A61B 5/02* (2006.01)
(52) U.S. Cl. .......................... 600/528; 607/4
(58) Field of Classification Search .............. 607/4, 18; 600/439, 485, 500, 513, 514, 528
    See application file for complete search history.

(56) References Cited

U.S. PATENT DOCUMENTS

| 4,094,308 A | 6/1978 | Cormier |
| 4,289,141 A | 9/1981 | Cormier |
| 4,446,872 A | 5/1984 | Marsoner et al. |
| 4,548,204 A | 10/1985 | Groch et al. |
| 4,649,930 A | 3/1987 | Groch et al. |
| 4,763,646 A | 8/1988 | Lekholm |
| 4,905,706 A | 3/1990 | Duff et al. |
| 4,915,113 A | 4/1990 | Holman |
| 4,989,611 A | 2/1991 | Zanetti et al. |
| 5,159,932 A | 11/1992 | Zanetti et al. |
| 5,365,932 A | 11/1994 | Greenhut |
| 5,496,361 A | 3/1996 | Moberg et al. |
| 5,540,727 A | 7/1996 | Tockman et al. |
| 5,554,177 A * | 9/1996 | Kieval et al. ............ 607/17 |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,792,195 A | 8/1998 | Carlson et al. |
| 5,836,987 A | 11/1998 | Baumann et al. |

(Continued)

FOREIGN PATENT DOCUMENTS

WO    WO-2004035137 A1    4/2004

(Continued)

OTHER PUBLICATIONS

"International Application Serial No. PCT/US2008/004832, International Search Report mailed Sep. 3, 2008", 4 pgs.

(Continued)

*Primary Examiner* — Carl H Layno
*Assistant Examiner* — Pamela M Bays
(74) *Attorney, Agent, or Firm* — Schwegman, Lundberg & Woessner, P.A.

(57) ABSTRACT

A system and method to sense heart sounds with one or more implantable medical devices according to one or more parameters. The system alters one or more of the parameters as a function of one or more triggering events. The system then senses heart sounds with the one or more implantable medical devices according to at least the one or more altered parameters.

17 Claims, 8 Drawing Sheets

U.S. PATENT DOCUMENTS

| | | |
|---|---|---|
| 5,935,081 A | 8/1999 | Kadhiresan |
| 5,991,661 A | 11/1999 | Park et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,077,227 A | 6/2000 | Miesel et al. |
| 6,152,884 A | 11/2000 | Bjorgaas |
| 6,264,611 B1 | 7/2001 | Ishikawa et al. |
| 6,298,269 B1 | 10/2001 | Sweeney |
| 6,312,378 B1 | 11/2001 | Bardy |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,440,082 B1 | 8/2002 | Joo et al. |
| 6,477,406 B1 | 11/2002 | Turcott |
| 6,527,729 B1 | 3/2003 | Turcott |
| 6,575,916 B2 | 6/2003 | Halleck et al. |
| 6,643,548 B1 | 11/2003 | Mai et al. |
| 6,650,940 B1 | 11/2003 | Zhu et al. |
| 6,665,564 B2 | 12/2003 | Lincoln et al. |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 7,052,466 B2 | 5/2006 | Scheiner et al. |
| 7,115,096 B2 | 10/2006 | Siejko et al. |
| 7,123,962 B2 | 10/2006 | Siejko et al. |
| 7,174,203 B2 | 2/2007 | Arand et al. |
| 7,853,327 B2 | 12/2010 | Patangay et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0055352 A1 | 3/2003 | Hayek et al. |
| 2003/0069608 A1 | 4/2003 | Sweeney |
| 2003/0072458 A1 | 4/2003 | Halleck et al. |
| 2003/0093002 A1 | 5/2003 | Kuo |
| 2003/0093003 A1 | 5/2003 | Watrous et al. |
| 2003/0120159 A1 | 6/2003 | Mohler |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0127792 A1* | 7/2004 | Siejko et al. .................. 600/439 |
| 2004/0138572 A1 | 7/2004 | Thiagarajan |
| 2004/0167417 A1* | 8/2004 | Schulhauser et al. ......... 600/513 |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1* | 12/2004 | Arand et al. .................. 600/528 |
| 2005/0027323 A1 | 2/2005 | Mulligan et al. |
| 2005/0033190 A1 | 2/2005 | Bauer |
| 2006/0020294 A1 | 1/2006 | Brockway et al. |
| 2006/0247550 A1 | 11/2006 | Thiagarajan et al. |
| 2007/0191725 A1 | 8/2007 | Nelson |
| 2011/0077543 A1 | 3/2011 | Patangay et al. |

FOREIGN PATENT DOCUMENTS

WO    WO-2008/130532 A1    10/2008

OTHER PUBLICATIONS

"International Application Serial No. PCT/US2008/004832, Written Opinion mailed Sep. 3, 2008", 7 pgs.

Dreuw, P., et al., "Tracking Using Dynamic Programming for Appearance-Based Sign Language Recognition", *Proceedings of the 7th International Conference on Automatic Face and Gesture Recognition*, (2006), 293-298.

"U.S. Appl. No. 11/736,055 Notice of Allowance mailed Aug. 13, 2010", 8 pgs.

"U.S. Appl. No. 11/736,055, Non-Final Office Action mailed Mar. 12, 2010", 8 pgs.

"U.S. Appl. No. 11/736,055, Response filed Jul. 2, 2010 to Non Final Office Action mailed Mar. 12, 2010", 17 pgs.

* cited by examiner

ADAPTIVE SAMPLING OF HEART SOUNDS

TECHNICAL FIELD

Various examples relate to the field of implantable medical devices, and in an example, but not by way of limitation, to the adaptive sampling of heart sounds by implantable medical devices.

BACKGROUND

The heart is at the center of the circulatory system. It includes four chambers—two atria and two ventricles. The right atrium receives deoxygenated blood from the body, pumps it into the right ventricle, and the right ventricle pumps the blood to the lungs to be re-oxygenated. The re-oxygenated blood returns to the left atrium, it is pumped into the left ventricle, and then the blood is pumped by the left ventricle throughout the body to meet the hemodynamic needs of the body.

Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made during closure of the mitral and tricuspid valves. The second heart sound (S2) is made by the closure of the aortic and pulmonary valves. The third heart sound (S3) and fourth heart sound (S4) are often related to abnormal filling pressures of the left ventricle during diastole. Heart sounds are useful indications of proper or improper functioning of a patient's heart.

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical therapy or to aid a physician or caregiver in patient diagnosis through internal monitoring of a patient's condition, or both. The devices may include or be connected to electrodes in communication with circuitry to monitor electrical heart activity within a patient, and often include one or more other sensors to internally monitor other patient parameters. Other examples of implantable medical devices include implantable diagnostic devices, implantable insulin pumps, devices implanted to administer drugs to a patient, or implantable devices with neural stimulation capability.

Overview

An implantable medical device can be used to adaptively sample heart sounds. The heart sounds can be compared to independently specifiable thresholds, such as to trigger an alert or responsive therapy, or to display one or more trends. The heart sound information can also be combined with one or more other parameters or patient reported symptoms to generate a status indicator or to trigger an alarm or responsive therapy or to display one or more trends. The alert can notify a patient or a caregiver, such as via remote monitoring. The status indicators, alarms, therapy, display, or trend may be used, for example, to manage congestive heart failure (CHF).

In Example 1, a system includes an implantable medical device. The implantable medical device includes a control circuit; a parameter circuit, coupled to the control circuit, the parameter circuit including one or more parameters; a sensor, coupled to the control circuit, the sensor configured to sense energy and produce a signal indicative of heart sounds; a heart sound detector, coupled to the control circuit, the heart sound detector adapted to detect heart sounds within the signal; and a triggering circuit, coupled to the control circuit, the triggering circuit configured to transmit a signal to the control circuit upon the occurrence of a triggering event. The sensor senses energy or the heart sound detector detects heart sounds as a function of the one or more parameters. The triggering circuit signal causes a change in one or more of the parameters.

In Example 2, the sensor of Example 1 is optionally an acoustic sensor that senses acoustic energy and produces an acoustic signal.

In Example 3, the parameters of Examples 1-2 optionally include one or more of a sampling frequency, a data acquisition separation interval (also referred to as a data acquisition frequency), a data acquisition interval, one or more characteristics of an ensemble average, a bit resolution, a noise blanking interval, and a retry interval.

In Example 4, the triggering events of Examples 1-3 are optionally a function of one or more of a heart rate, a cardiac cycle phase, a respiration rate, a respiration phase, a posture, a time of day, a noise level, an activity level, a patient risk factor, a sleep state, a patient input, a care giver input, a body weight, a change in health status, a predetermined interval, a result of a prior data acquisition, a pacing status, a sensing status, a pressure level, an impedance, a heart rate variability, a heart sound amplitude, a heart sound interval, a heart sound duration, and a clinic visit.

In Example 5, the patient risk factor of Examples 1-4 optionally includes one of more of a heart failure decompensation risk factor, an increase in an occurrence or intensity of one or more of an S3 heart sound and an S4 heart sound, and an occurrence or change in a splitting of an S1 heart sound or an occurrence or change in a splitting of an S2 heart sound.

In Example 6, the triggering circuit of Examples 1-5 optionally transmits the signal as a function of one or more of an onset, a termination, an increase, a decrease, a presence, an absence, a probability of occurrence, a probability of frequency, and a rate of change of the one or more triggering events.

In Example 7, the systems of Examples 1-6 optionally include a telemetry circuit coupled to the control circuit, and an external device wirelessly coupled to the telemetry circuit. The telemetry circuit optionally transmits heart sound data to the external device as a function of the change in one or more of the parameters.

In Example 8, the systems of Examples 1-7 optionally include an external data base coupled to the external device, the external data base for receiving and storing the heart sound data.

In Example 9, the systems of Examples 1-8 optionally include a telemetry circuit coupled to the control circuit and a second implantable medical. The telemetry circuit optionally communicatatively couples the first and second implantable medical devices.

In Example 10, the systems of Examples 1-9 optionally include a therapy circuit, wherein the therapy circuit is configured to provide therapy to a patient.

In Example 11, the therapy circuit of Examples 1-10 is configured to provide one or more of pacing, defibrillation, cardioversion, cardiac resynchronization, and neural stimulation therapy.

In Example 12, a process includes sensing heart sounds with a first implantable medical device according to one or more parameters; altering one or more of the parameters as a function of one or more triggering events; and sensing heart sounds with the implantable medical device according to at least the one or more altered parameters.

In Example 13, the parameters of Example 12 optionally include altering one or more of a sampling frequency, a data acquisition separation interval, a data acquisition interval, one or more characteristics of an ensemble average, a bit resolution, a noise blanking interval, and a retry interval. The data acquisition separation, data acquisition, and retry intervals may be adapted according to other triggering parameters such as a detected change in posture.

In Example 14, the characteristics of the ensemble average of Examples 12-13 optionally include one or more of using only sensed heart beats, using only paced heart beats, selecting non-consecutive heart beats, the number of heart beats, and a threshold amplitude for heart beats.

In Example 15, the retry interval of Examples 12-14 is optionally a function of a result of a previous data acquisition.

In Example 16, the alteration of the sampling frequency of Examples 12-15 is optionally a function of a frequency characteristic of a particular heart sound to be sensed.

In Example 17, the data sampling interval of Examples 12-16 is optionally a function of a time period during a cardiac cycle when a particular heart sound is likely to be present.

In Example 18, the triggering events of Examples 12-17 are optionally a function of one or more of a heart rate, a cardiac cycle phase, a respiration rate, a respiration phase, a posture, a time of day, a noise level, an activity level, a patient risk factor, a sleep state, a patient input, a care giver input, a body weight, a patient health status, a predetermined interval, a result of a prior data acquisition, a pacing status, a sensing status, a pressure level, an impedance, and a clinic visit.

In Example 19, the patient risk factor of Examples 12-18 optionally include one or more of a heart failure decompensation risk factor, an increase in an occurrence or intensity of one or more of an S3 heart sound and an S4 heart sound, and an occurrence or change in a splitting of an S1 heart sound or an S2 heart sound.

In Example 20, the alteration of the one or more parameters as a function of the one or more triggering events of Examples 12-19 optionally includes using one or more of an onset, a termination, an increase, a decrease, a presence, an absence, and a rate of change of the one or more trigger events.

In Example 21, the processes of Examples 12-20 optionally include returning to the sensing of heart sounds according to a previous set of parameters upon a change in one or more of the triggering events.

In Example 22, the processes of Examples 12-21 optionally include one or more of terminating, initiating, increasing, and decreasing heart sound sampling or processing in response to the one or more triggering events.

In Example 23, the processes of Examples 12-22 optionally include comprising changing a processing location between the first implantable device and one or more of a second implantable device and an external device as a function of one or more of the triggering events.

In Example 24, the processes of Examples 12-23 optionally include telemetering heart sound data to one or more of another implantable device, an external device, and an external database as a function of one or more of the triggering events.

In Example 25, the processes of Examples 12-24 optionally include synchronizing the sensing of the heart sounds with a physiological event as a function of one or more of the triggering events.

In Example 26, the physiological event of Examples 12-25 optionally includes one or more of respiration, posture, sleep state, circadian rhythm, paced heart beats, sensed heart beats, and heart rate.

This overview is intended to provide an overview of the subject matter of the present patent application. It is not intended to provide an exclusive or exhaustive explanation of the disclosure. The detailed description is included to provide further information about the subject matter of the present patent application.

BRIEF DESCRIPTION OF THE DRAWINGS

In the drawings, which are not necessarily drawn to scale, like numerals describe similar components throughout the several views. The drawings illustrate generally, by way of example, but not by way of limitation, various examples discussed in the present document.

DETAILED DESCRIPTION

The following detailed description refers to the accompanying drawings which form a part hereof, and in which is shown by way of illustration specific examples in which the disclosure may be practiced. These examples, which are sometimes referred to as examples, are discussed in sufficient detail to enable those skilled in the art to practice the teachings of the disclosure, and such examples may be combined, or other examples may be utilized, and structural, logical and electrical changes may be made without departing from the scope of the present disclosure. The following detailed description provides examples, and the scope of the present disclosure is defined by the appended claims and their equivalents.

It should be noted that references to "an", "one", or "various" examples in this disclosure are not necessarily to the same example, and such references contemplate more than one example.

This document describes adaptive sampling of heart sounds. In this disclosure, the term heart sound is meant to include any sound or vibration generated by the heart, and/or blood flowing through the heart, including, but not limited to one or more of an S1 heart sound, an S2 heart sound, an S3 heart sound, an S4 heart sound, a regurgitant heart murmur, a stenotic heart murmur sound, and a coronary vascular blood turbulence sound. The term cardiogenic sounds is sometimes used to generically refer to heart sounds.

Figure 1:
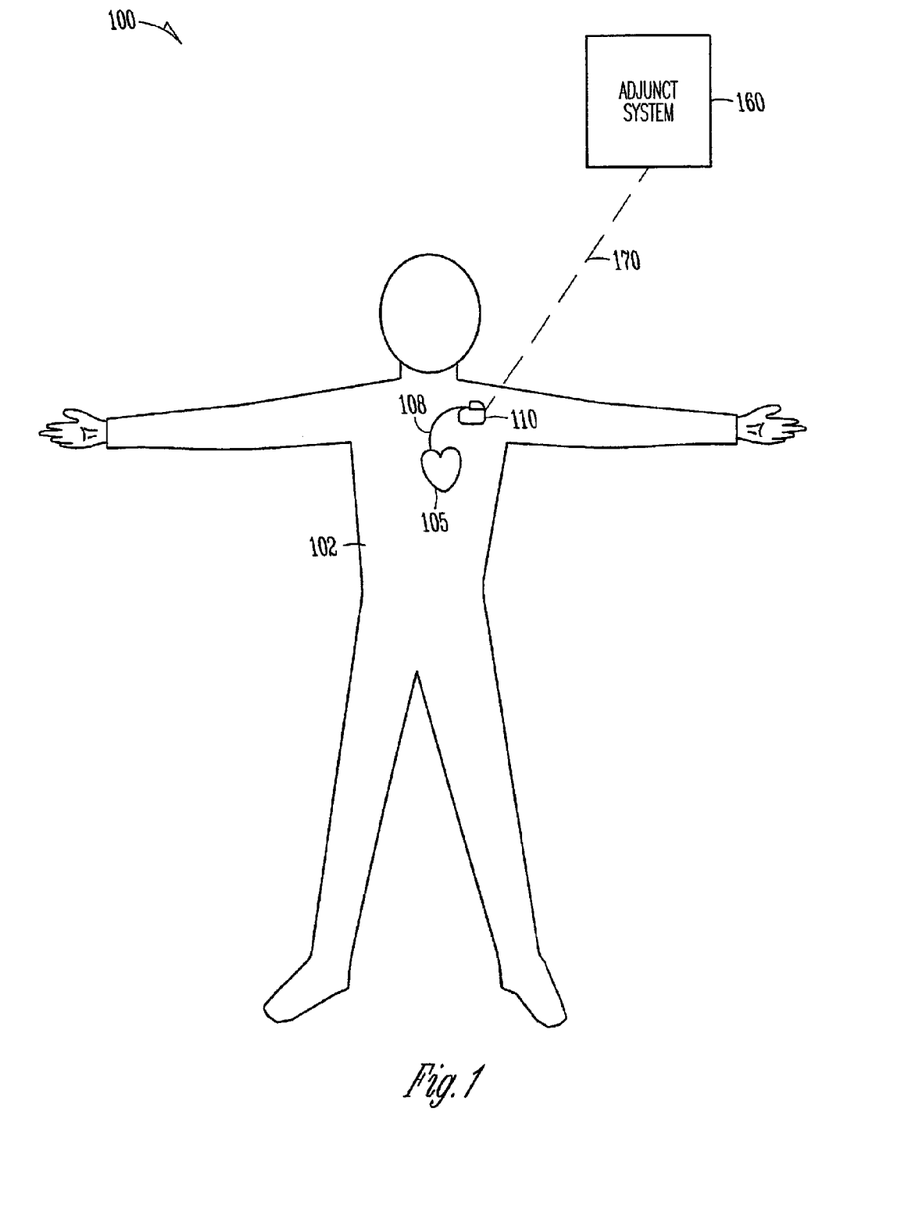
FIG. 1 illustrates an example of an implanted medical device coupled to an adjunct external device.
Figure 6:
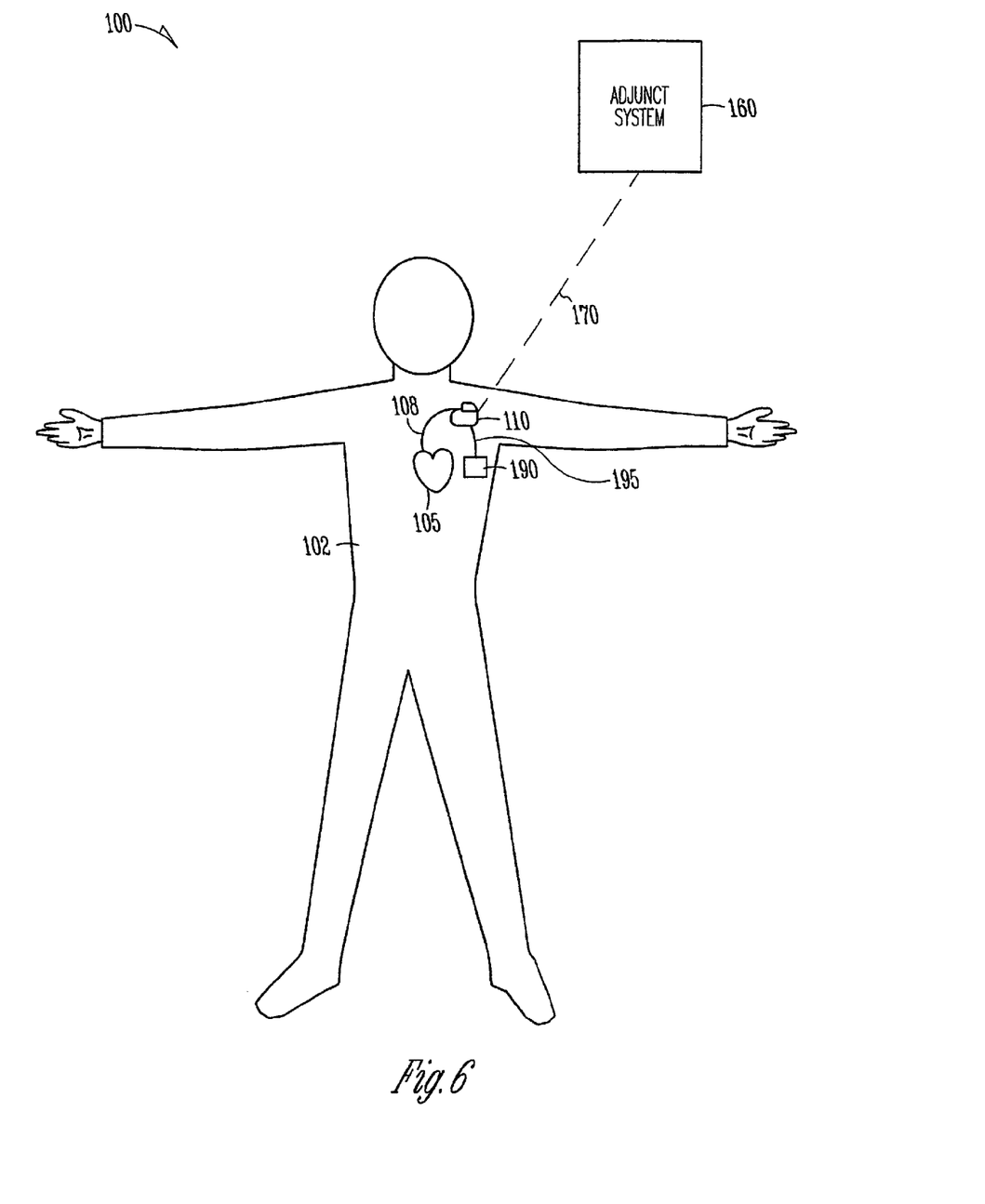
FIG. 6 illustrates an example of a first implantable medical device and a second implantable medical device coupled to an adjunct external device.
Figure 7:
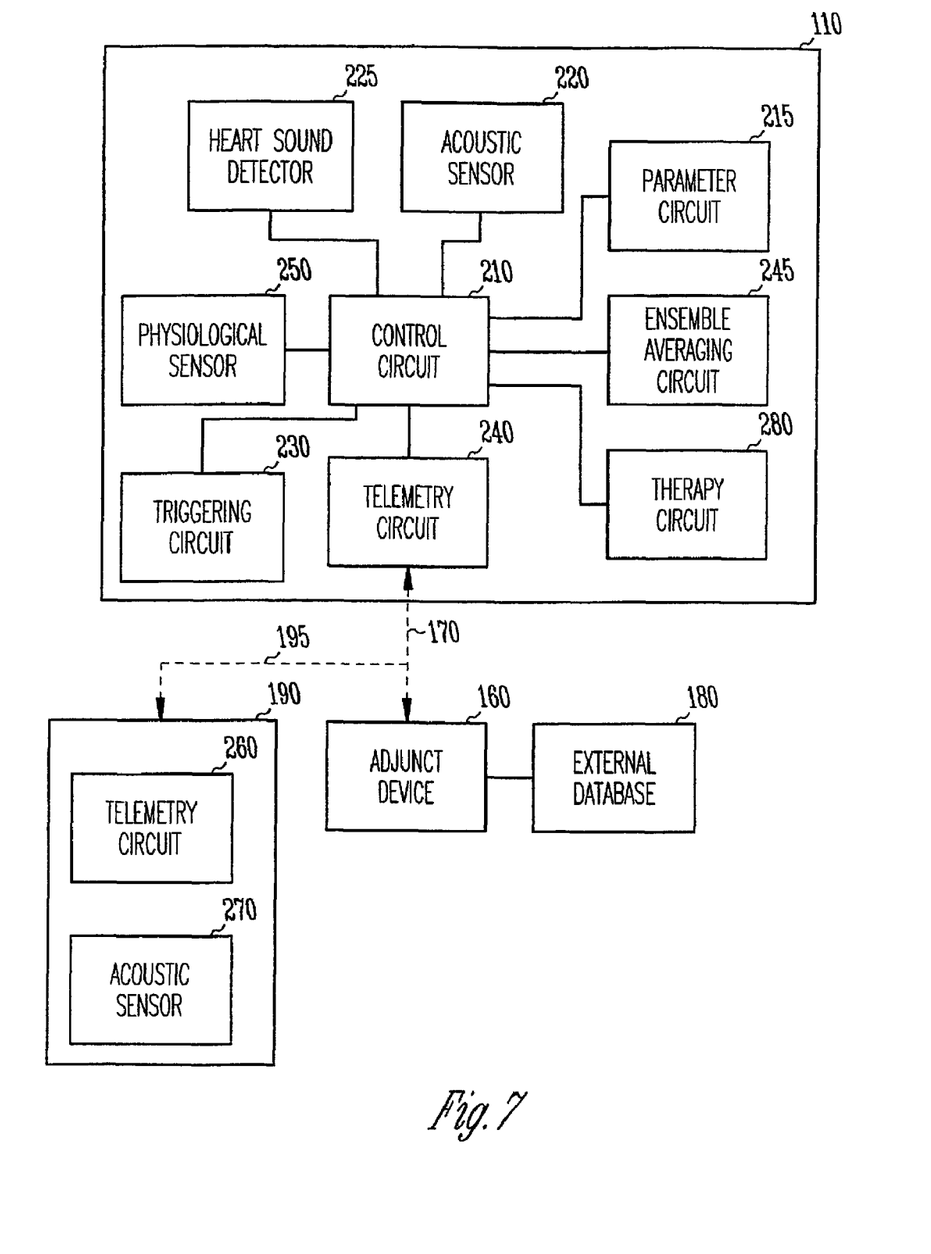
FIG. 7 illustrates a block diagram of a first implantable medical device and a second implantable medical device.

FIG. 1 is a diagram illustrating an example of a medical device system 100 which can be used in connection with transmitting data from an implantable device 110 to an adjunct system 160. In an example, the adjunct system 160 is an external (non-implanted) system. FIG. 1 further illustrates a body 102 with a heart 105. In this example, the system 100 includes the implantable medical device 110, a lead system 108, the adjunct system 160, and a wireless telemetry link 170. Data and/or other instructions may be transferred between the device 110 and the adjunct device 160 via the telemetry link 170. FIGS. 6 and 7 illustrate that the implantable medical device 110 may be coupled to a second implantable medical device 190 via an intra-body communication link 195. The device 190 may include a telemetry circuit 260 and an acoustic sensor 270. The acoustic sensor 270 may be used in addition to, or instead of, the acoustic sensor 220. Data that is transferred between the device 110 and the adjunct device 160 may include data input to and/or data output from a patient or care giver via the telemetry circuit 260 of the second implantable device 190. Examples of care givers include physicians, nurses, and relatives, friends or other assistants of the patient.

Figure 2:
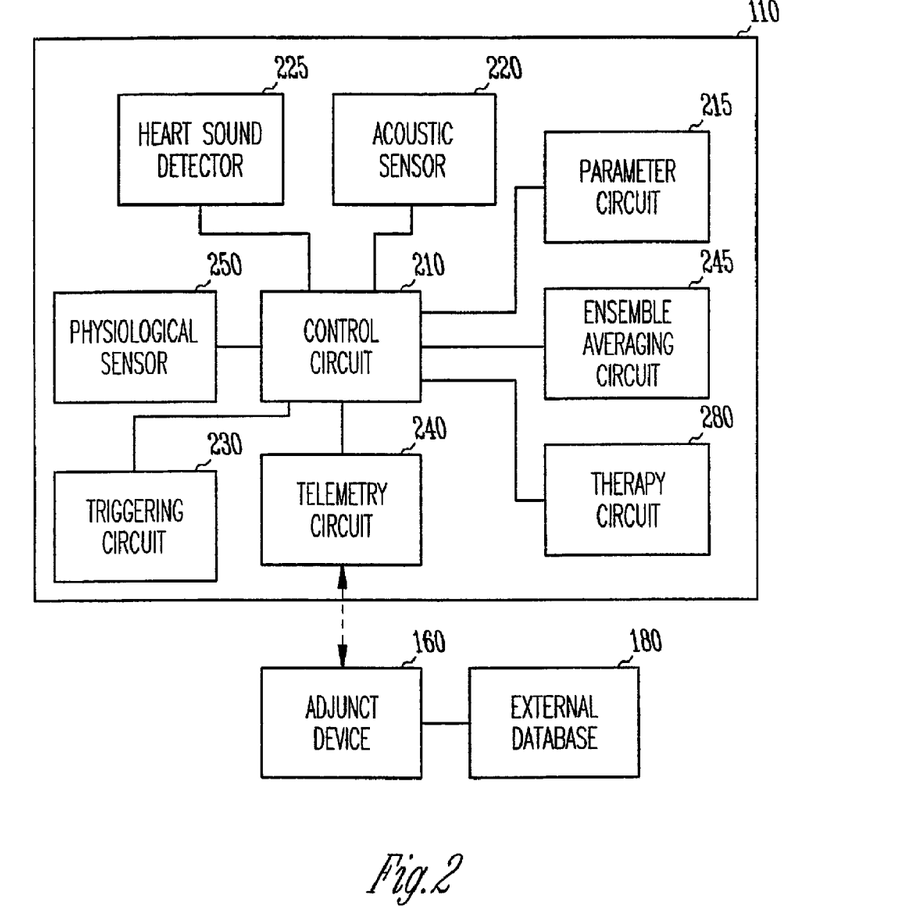
FIG. 2 illustrates a block diagram of an implantable medical device.

FIG. 2 illustrates an example of an implantable medical device 110. In this example, the device 110 includes a control circuit 210, which can include or can be coupled to a parameter circuit 215. The parameter circuit 215 may include one or more parameters. Some of these parameters may be used to determine how the device 110 obtains heart sounds. An acoustic sensor 220 is coupled to the control circuit 210. The acoustic sensor 220 may include any sensor suitable for this purpose including an accelerometer, a microphone, or some other type of acoustic-to-electrical, acoustic-to-optical or other acoustic transducer. The acoustic sensor 220 senses acoustic vibration energy and generates a responsive signal as a function of the acoustic vibration energy. The responsive signal produced by the acoustic sensor may be indicative of a heart sound. A heart sound detector 225 is coupled to or included in the control circuit 210. The heart sound detector 225 detects heart sounds in the responsive signal generated by the acoustic sensor 220. In an example, the acoustic sensor 220 senses acoustic energy and/or the heart sound detector 225 detects heart sounds as a function of the one or more parameters stored in the parameter circuit 215. A triggering circuit 230 is coupled to or included in the control circuit 210. A triggering signal generated by the triggering circuit 230 may cause a change in one or more of these heart sound acquisition or processing parameters, thereby changing how the implanted device 110 obtains information indicative of heart sounds produced by the heart. The parameters may also be altered directly by the control circuit 210, or by another component of the device 110 in conjunction with the control circuit 210. The device 110 may further be configured to include a therapy circuit 280 coupled to the control circuit 210. The therapy circuit 280 may be configured to provide one or more of pacing, defibrillation, cardioversion, cardiac resynchronization, and neural stimulation therapy.

In this example, a physiological sensor 250 is coupled to the control circuit 210, such as via a wired or wireless connection. Examples of the physiological sensor 250 may include a heart rate sensing circuit, a respiration rate sensing circuit, a respiration phase sensing circuit, a posture sensing circuit, a sleep detector circuit, a blood pressure sensing circuit, and/or a cardiac impedance sensing circuit. One or more of the physiological sensors 250 may be part of the implantable medical device 110. For example, if the implantable medical device includes a cardiac pacer, then the pacer may also include a heart rate sensing circuit.

FIG. 2 illustrates that the implantable medical device 110 may further include a telemetry circuit 240, such as coupled to the control circuit 210. The telemetry circuit 240 wirelessly communicatively couples the implantable medical device 110 to the adjunct or external device 160. In an example, the telemetry circuit 240 may transmit heart sound data to the external device 160, for example, as a function of the change in one or more of the parameters in the parameter circuit 215. FIG. 2 further illustrates an example in which a remote or local external database 180 may be coupled to the external device 160. The external database 180 may be used for storing data including heart sound data received from the implantable medical device 110.

FIG. 2 further illustrates an example in which the implantable medical device 110 may include an ensemble averaging circuit 245 or other central tendency or lowpass filtering circuit. While it is referred to as an ensemble averaging circuit, such a circuit is not limited to the calculation of a simple statistical average, but also is meant to encompass one or more other statistical or other measures such as, for example, a weighted mean, a median, or a mode. The ensemble averaging circuit 245 may calculate an ensemble average for an acoustic signal, a heart sound signal, or any other signal sensed by the device 110.

The one or more parameters stored within the parameter circuit 215 may include one or more parameters that control the manner in which heart sounds are obtained by the device 110. Examples of such parameters may include a sampling frequency, a data acquisition separation interval, a data acquisition interval, one or more characteristics of an ensemble average, a bit resolution, a noise blanking interval, and a retry interval. In certain examples, the sampling frequency parameter controls the frequency (i.e., samples per second) at which data points are sampled in an analog signal waveform including heart sound information in order to generate a sampled or digital signal of the waveform. The data acquisition separation interval generally relates to the time period separating different data acquisition periods (e.g., sampling a buffer of heart sound data every 15 minutes), or how often a buffer of multiple heart beats is updated with newly acquired data. The data acquisition interval is generally the actual time period during which a buffer of heart sounds is acquired. For example, the device 110 may sample a set of consecutive heart sounds for 30 seconds. The data acquisition interval may also be referred to as the acquisition buffer length. The bit resolution generally refers to the number of bits representing each sample point. In an example, the bit resolution is 8 bits. In another example, the bit resolution is 16 bits. The noise blanking interval generally refers to a time period during which heart sound data acquisition does not occur (e.g., because it is automatically inhibited). For example, heart sound data acquisition may be automatically inhibited during time periods of increased patient activity, which could result in higher noise interfering with the heart sound data acquisition. The noise blanking interval may also refer to a particular segment of the cardiac cycle during which the device inhibits or ignores acquired heart sound data (e.g., the first 50 ms of the cardiac cycle), such as to ignore periods of time during which useful heart sound information is not likely to be present. The retry interval generally relates to the amount of time that the device will wait before it attempts to acquire more heart sound data after an unsuccessful attempt at acquiring heart sound data (e.g., because of a noisy signal). The control circuit 210 and/or the triggering circuit 230 uses one or more of these parameters to control operation of one or more of the acoustic sensor 220, the heart sound detector 225, the telemetry circuit 240, and the ensemble averaging circuit 245, such as in the acquisition or processing of heart sound data.

One or more of these heart sound parameters that determine the manner of the acquisition or processing of heart sounds, such as by the implantable device 110, may be altered by one or more triggering events, yielding adaptive heart sound acquisition or processing. In various examples, such triggering events may be determined as a function of one or more of a heart rate, a cardiac phase, a respiration rate, a respiration phase, a posture, a time of day, a noise level, an activity level, a patient risk factor, a sleep state, a patient input, a physician input, a body weight, a change in health status, a predetermined interval, a result of a prior data acquisition, a pacing status, a sensing status, a pressure level, an impedance, or a clinic visit.

The device 110 can be configured to adaptively change any aspect of the manner in which it acquires heart sound information (e.g., the sampling frequency, the sampling interval, etc.) as a function of any one or more of the triggering events. This can be based on either a change in the triggering event parameter (e.g., an increase in the heart rate), the presence of a particular triggering event (e.g., the body is in the prone or supine positions, triggering heart sound data acquisition), the triggering event being below or above a threshold (e.g., the level of noise in the system or environment is below a certain level), and/or a triggering event parameter that is within a certain range (e.g., acquire heart sound information between 12:00 p.m. and 4 p.m.). Therefore, the triggering event may include one or more of an onset, a termination, an increase, a decrease, a presence, an absence, and a rate of change of the one or more triggering event parameters.

In another example, the automatic triggering event may include an identified patient risk factor, such as one or more of a heart failure decompensation risk factor, an increase in an occurrence or intensity of one or more of an S3 heart sound or an S4 heart sound, an occurrence or change in a time-splitting of an S1 heart sound or an S2 heart sound, and a population risk stratifier. The heart failure decompensation risk factor can include one or more of, for example, an increased respiration rate, a decreased thoracic impedance, and an increased resting heart rate. Similarly, an onset or an increase in the intensity of an S3 or an S4 heart sound are risk factors, and the manner in which heart sound information is obtained by a device may be altered as a function of the onset or increase in the intensity of the S3 and/or S4 heart sounds. Similarly, an occurrence or change in a splitting of an S1 heart sound or an occurrence or a change in a splitting of an S2 heart sound are risk factors, and heart sound data acquisition may be adapted accordingly. Also, if there is a change in the patient's general health or metabolic need status (indicated by, for example, an increase in the patient's resting heart rate), then the current data acquisition interval may not be at a sufficient rate, and the data acquisition interval may be shortened, so that more buffers are collected during a particular time period. Similarly, the data sampling interval may be lengthened, so that more heart beats are collected in a buffer. Alternatively, if the patient's general health status is improving, the sampling frequency may be decreased.

Figure 3:
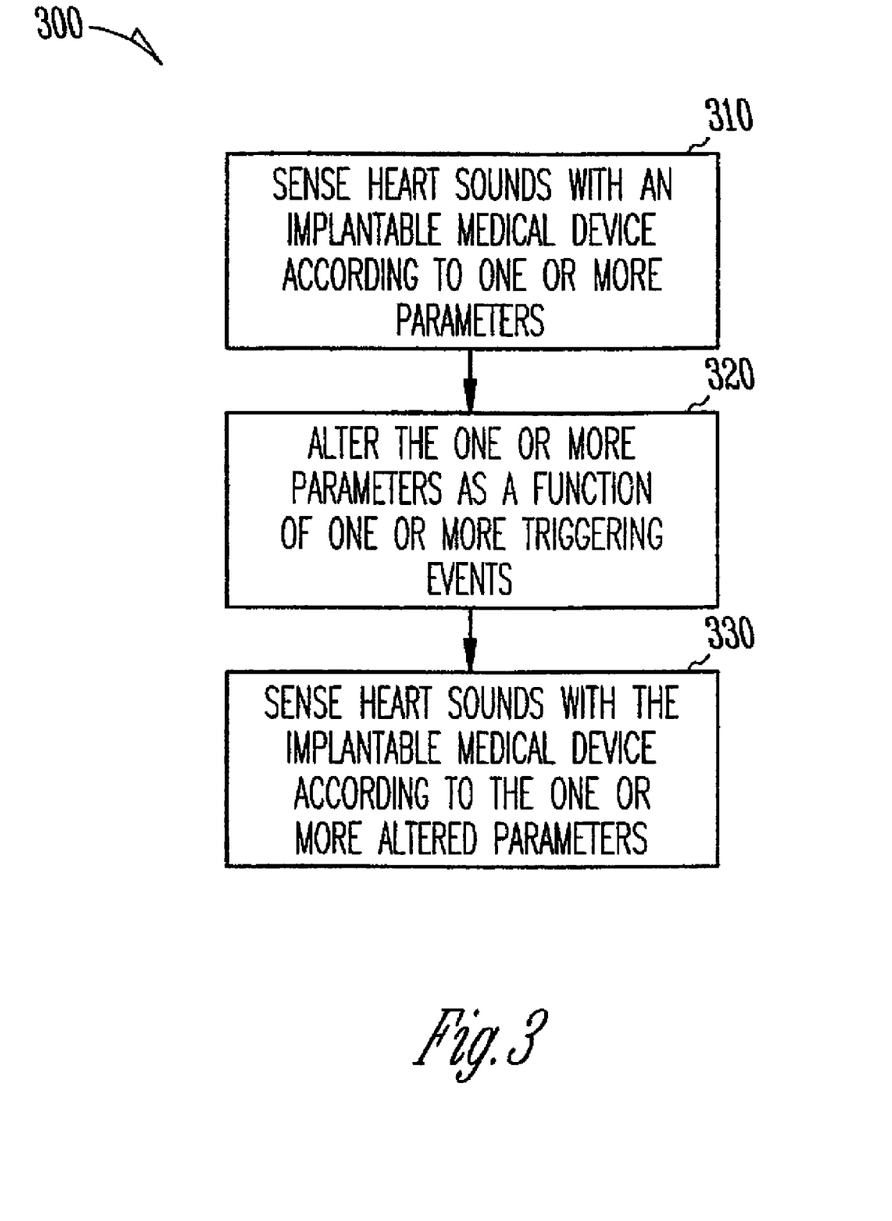
FIG. 3 illustrates a flowchart of an example process to adaptively sample heart sounds.

FIG. 3 illustrates an example of a process 300 for the adaptive sampling of heart sounds by an implantable device. At 310, the process senses heart sounds with an implantable medical device according to one or more parameters. At 320, the one or more parameters are altered as a function of one or more triggering events. Lastly, at 330, heart sounds are sensed with the implantable medical device according to at least the one or more altered parameters.

Figure 4A:
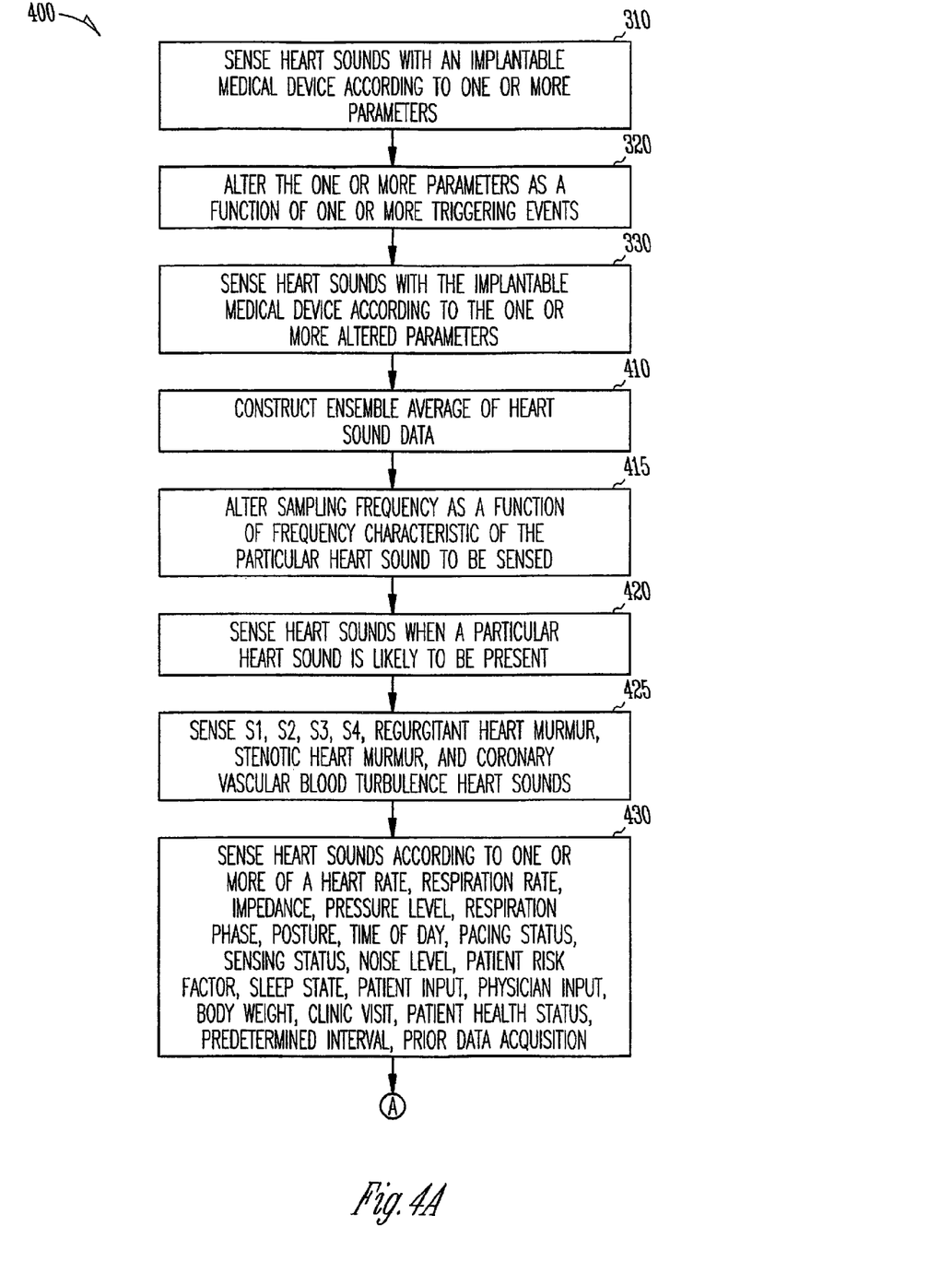
FIGS. 4A and 4B illustrate a flowchart of another example process to adaptively sample heart sounds.
Figure 4B:
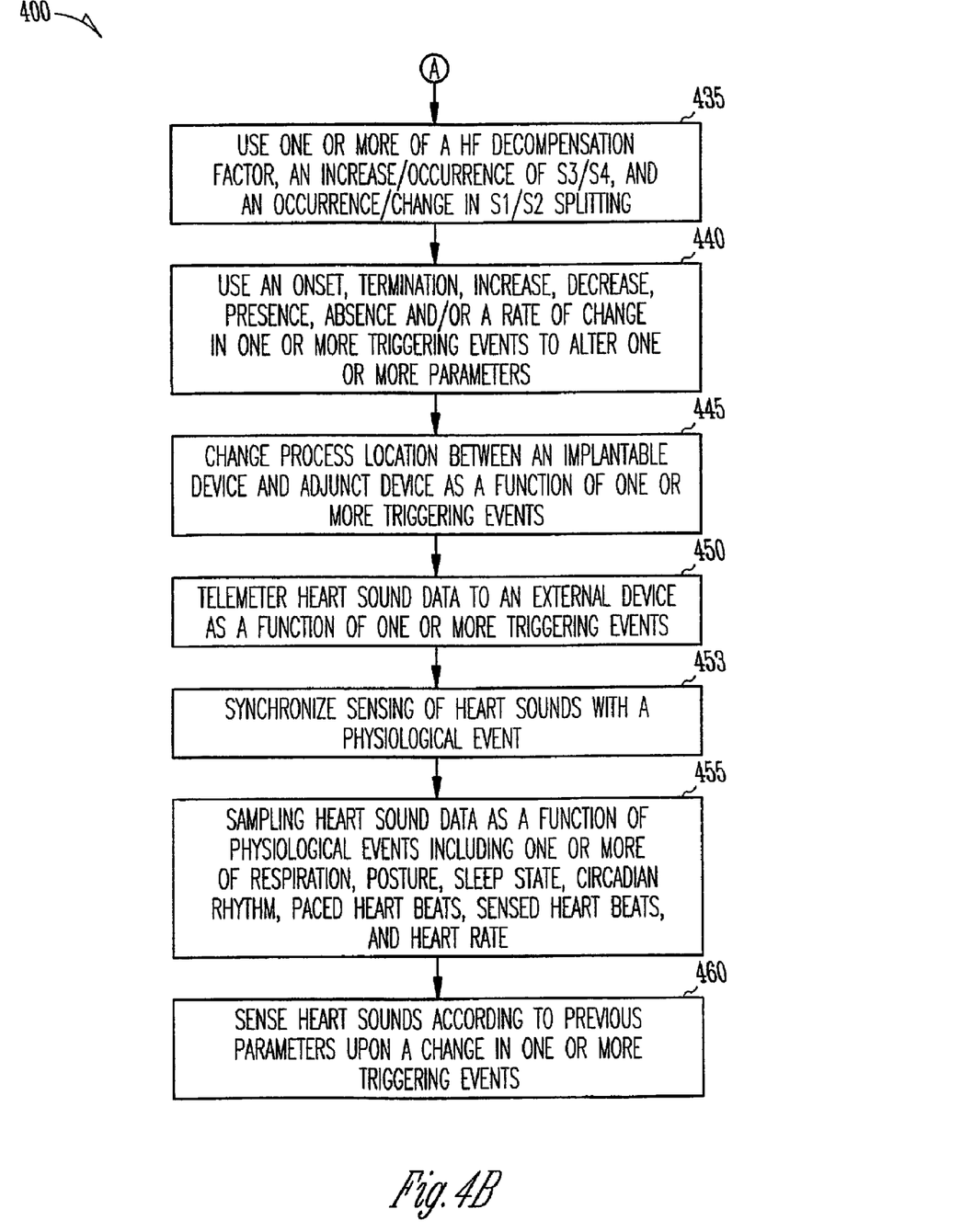

FIGS. 4A and 4B illustrate another example of a process 400 for the adaptive sampling of heart sounds by an implantable device. As indicated in FIGS. 4A and 4B, the process 400 may include at 310 sensing heart sounds with an implantable medical device according to one or more parameters. At 320, the one or more parameters are altered as a function of one or more triggering events. At 330, heart sounds are sensed with the implantable medical device according to at least the one or more altered parameters.

At 410, heart beats that are sensed during a particular data sampling interval are ensemble averaged before further analysis is performed on the data. This conditions the signal by removing noise and compressing the data. An ensemble average for a buffer of heart sound signals may be generated or represented by a summation of the accelerometer (or other acoustic sensing device) outputs relative to a reference point such as a V-event marker. Using an ensemble average in the adaptive sampling of heart sounds also permits the system and method to select certain cardiac cycles in a buffer for retention, processing, and storage, and permits discarding of other cardiac cycles in a buffer.

Figure 5:
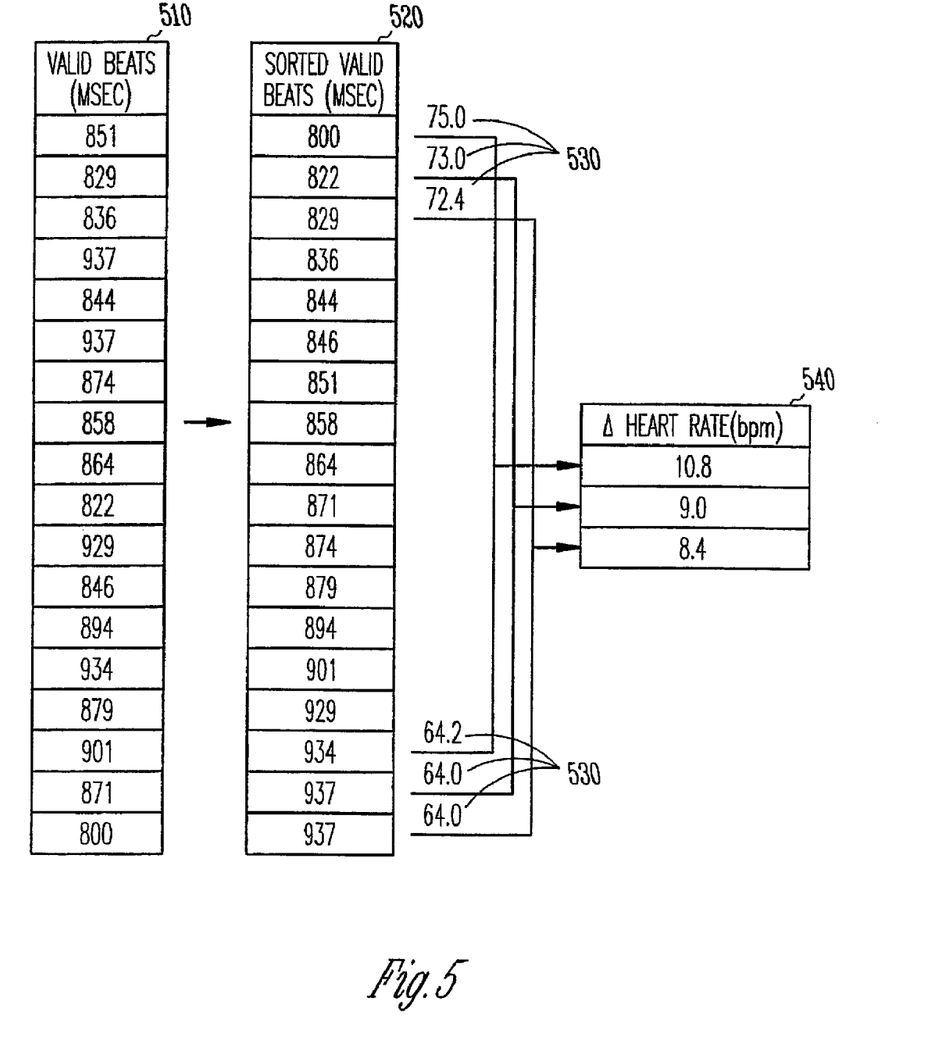
FIG. 5 illustrates an example ensemble averaging technique.

An example of a method of selecting particular cardiac cycles, or heart beats, for an ensemble average is illustrated in FIG. 5. FIG. 5 illustrates a buffer of heart beat data 510. The heart beat data 510 includes the duration of each heart beat in milliseconds. In the example of FIG. 5, the heart beat data 510 includes the duration of 18 separate heart beats. The heart beats in the buffer are then sorted in ascending order of heart beat duration as illustrated in 520. The heart beat durations are converted to heart rates 530 by taking the reciprocal of the duration, and a difference 540 is calculated between the heart rate of a first heart beat in a set of 16 consecutive ordered heart beats and the heart rate of a $16^{th}$ beat in the set of 16 consecutive heart beats. This calculation is performed for all the sets of 16 consecutive heart beats in the buffer, and the set of ordered heart beats with the smallest change in rate between the first heart beat in the set of 16 consecutive beats and the $16^{th}$ heart beat in a set of 16 consecutive beats is selected as the beats to retain, process, and store. By initially sorting the beats in ascending duration order, and determining the ordered beats with the smallest change in heart rate, the process is able to select the "best" non-consecutive beats for the calculation of the ensemble average. While the example of FIG. 5 illustrates the selection of 16 consecutive heart beats from a buffer of 18 consecutive hearts beats, other buffer sizes may be used and other numbers of consecutive heart beats may be selected.

Additionally or alternatively, the number of beats that may be selected to construct an ensemble average may be altered according to the amount of noise detected in the system and the time allowed for acquisition of the heart sounds. For example, if the noise increases, it may be necessary to increase the number of beats that are included in each ensemble average. As another example, if the use of the heart sound data by the device 110 requires accelerated processing, the device may be configured to reduce the number of heart beats sampled for an ensemble average, thereby reducing the time required to generate the ensemble average.

In a particular example of calculating an ensemble average, only sensed heart beats are used. In another example, only paced heart beats are used. In another example, a certain specified number of cardiac beats must be present in the data buffer to calculate the ensemble average. If that minimum number of beats is present in the buffer, the first beats in the buffer may be selected for the calculation of the ensemble average, and the rest of the beats in the buffer may be discarded. In another example, there is a threshold condition imposed upon the heart sound amplitude in order for a heart beat to be considered for the ensemble average. Any or all of these ensemble averaging factors may be altered by one or more of the triggering events discussed above.

At 415, the sampling frequency is altered as a function of a frequency characteristic of a particular heart sound to be sensed. For example, if the desire is to sense the S3 heart sound with the implantable device, then the sampling frequency may be set to 10-30 Hz. This may either be done manually by a health care provider, or done by the device 110 in response to an occurrence or an increase in the S3 heart sound. In another embodiment, the sampling frequency for S3 may be around 50 Hz for Nyquist purposes. By comparison, if it is desired to sample the S1 heart sound, a sampling frequency of 20-50 Hz may be more appropriate (or up to 100 Hz for Nyquist purposes). Moreover, depending on the condition of the patient, the device 110 may adaptively alter between the sampling frequencies of approximately 10-30 Hz and 20-50 Hz, or other frequencies that are associated with other heart sounds.

At 420, heart sounds are sensed during a specific time when a particular heart sound is likely to be present. For example, if it is desired to sense the S3 heart sound, then the sampling may be attempted at approximately 500-600 ms into the cardiac cycle. The sampling may be adjusted based on the heart rate. At 425, the heart sounds that are sensed include one or more of an S1 heart sound, an S2 heart sound, an S3 heart sound, an S4 heart sound, a regurgitant heart murmur, a stenotic heart murmur sound, and a coronary vascular blood turbulence sound.

At 430, the device uses one or more triggering events that are a function of one or more of a heart rate, a cardiac cycle phase, a respiration rate, a respiration phase, a posture, a time of day, a noise level, an activity level, a patient risk factor, a sleep state, a patient input, a physician input, a body weight, a patient health status, a predetermined interval, a result of a prior data acquisition, a pacing status, a sensing status, a pressure level, an impedance, and a clinic visit.

At 435, the device 110 uses as patient risk factors one or more of a heart failure decompensation factor, an increase in an occurrence or intensity of one or more of an S3 heart sound and an S4 heart sound, and an occurrence or change in a splitting of an S1 heart sound or an occurrence or change in an S2 heart sound.

At 440, the device, in altering of the one or more parameters as a function of the one or more triggering events includes using one or more of an onset, a termination, an increase, a decrease, a presence, an absence, and a rate of change of the one or more trigger events.

At 445, the process changes a processing location between the implantable device and an external device as a function of one or more of the triggering events. Similarly, at 450, the process telemeters heart sound data to one or more of an external device and an external database as a function of one or more of the triggering events. At 453, the process synchronizes the sensing of the heart sounds with a physiological event as a function of one or more of the triggering events. At 455, the physiological event includes one or more of respiration, posture, sleep state, circadian rhythm, paced heart beats, sensed heart beats, and heart rate. At 460, the device returns to sensing heart sounds according to a previous set of parameters upon a change in one or more of the triggering events.

In the foregoing detailed description, various features are grouped together in one or more examples or examples for the purpose of streamlining the disclosure. This method of disclosure is not to be interpreted as reflecting an intention that the claimed examples of the invention require more features than are expressly recited in each claim. Rather, as the following claims reflect, inventive subject matter lies in less than all features of a single disclosed example. Thus the following claims are hereby incorporated into the detailed description of examples of the invention, with each claim standing on its own as a separate example. It is understood that the above description is intended to be illustrative, and not restrictive. It is intended to cover all alternatives, modifications and equivalents as may be included within the scope of the invention as defined in the appended claims. Many other examples will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

As used in this disclosure, the term "circuit" is broadly meant to refer to hardware, software, and a combination of hardware and software. That is, a particular function may be implemented in specialized circuits, in software executing on general processor circuits, and/or a combination of specialized circuits, generalized circuits, and software.

The abstract is provided to comply with 37 C.F.R. 1.72(b) to allow a reader to quickly ascertain the nature and gist of the technical disclosure. The Abstract is submitted with the understanding that it will not be used to interpret or limit the scope or meaning of the claims.

The invention claimed is:

1. A system comprising:
 a first implantable medical device comprising:
  a control circuit;
  a sensor, coupled to the control circuit, the sensor configured to sense energy and produce a signal indicative of heart sounds;
  a heart sound detector, coupled to the sensor and the control circuit, the heart sound detector adapted to detect heart sounds within the signal indicative of heart sounds;
  a parameter circuit, coupled to the control circuit, the parameter circuit configured to store one or more heart sound signal processing parameters, wherein the device acquires and processes heart sound information as a function of the one or more heart sound signal processing parameters, wherein the heart sound signal processing parameter includes one or more of a sampling frequency, a data acquisition interval, one or more characteristics of an ensemble average, a bit resolution, a noise blanking interval, and a retry interval;
  a triggering circuit, coupled to the control circuit, the triggering circuit configured to transmit a triggering circuit signal to the control circuit upon device detection of a physiologic triggering event, and
  wherein the control circuit is configured to change one or more of the heart sound signal processing parameters in response to receipt of the triggering circuit signal.

2. The system of claim 1, wherein the sensor is an acoustic sensor that senses acoustic energy and produces an acoustic signal.

3. The system of claim 1, wherein the one or more triggering events is a function of one or more of a heart rate, a cardiac cycle phase, a respiration rate, a respiration phase, a posture, a time of day, a noise level, an activity level, a patient risk factor, a sleep state, a body weight, a change in health status, a predetermined interval, a result of a prior data acquisition, a pacing status, a sensing status, a pressure level, an impedance, a heart rate variability, a heart sound amplitude, a heart sound interval, and a heart sound duration.

4. The system of claim 3, wherein the patient risk factor includes one of more of a heart failure decompensation risk factor, an increase in an occurrence or intensity of one or more of an S3 heart sound and an S4 heart sound, and an occurrence or change in a splitting of an S1 heart sound or an occurrence or change in a splitting of an S2 heart sound.

5. The system of claim 1, wherein the triggering circuit transmits the signal as a function of one or more of an onset, a termination, an increase, a decrease, a presence, an absence, a probability of occurrence, a probability of frequency, and a rate of change of the one or more triggering events.

6. The system of claim 1, further comprising:
a telemetry circuit coupled to the control circuit; and
an external device wirelessly coupled to the telemetry circuit;
wherein the telemetry circuit is configured to include one or more of the functions of transmitting and receiving one or more of data related to the use of and acquisition of heart sound data.

7. The system of claim 6, further comprising an external data base coupled to the external device, the external data base for receiving and storing the heart sound data.

8. The system of claim 1, further comprising:
a telemetry circuit coupled to the control circuit; and
a second implantable medical device;
wherein the telemetry circuit communicatively couples the first and second implantable medical devices.

9. The system of claim 8, further comprising a therapy circuit, wherein the therapy circuit is configured to provide therapy to a patient.

10. The system of claim 9, wherein the therapy circuit is configured to provide one or more of pacing, defibrillation, cardioversion, cardiac resynchronization, and neural stimulation therapy.

11. A system comprising:
a first implantable medical device comprising:
a control circuit;
a sensor, coupled to the control circuit, the sensor configured to sense energy and produce a signal indicative of heart sounds;
a heart sound detector, coupled to the sensor and the control circuit, the heart sound detector adapted to detect heart sounds within the signal indicative of heart sounds;
a parameter circuit, coupled to the control circuit, the parameter circuit configured to store one or more heart sound signal processing parameters, wherein the device acquires and processes heart sound information as a function of the one or more heart sound signal processing parameters;
a triggering circuit, coupled to the control circuit, the triggering circuit configured to transmit a triggering circuit signal to the control circuit upon device detection of a physiologic triggering event, and
wherein the control circuit is configured to:
identify a specified heart sound to sense according to the detected physiologic triggering event; and
change a signal sampling frequency based on the identified heart sound.

12. The system of claim 11, wherein the control circuit is configured to select a first signal sampling frequency if the identified heart sound is an S3 heart sound and select a second different signal sampling frequency if the identified heart sound is an S1 heart sound.

13. The system of claim 11, wherein the control circuit is configured to select a first signal sampling frequency for the identified heart sound at a first determined heart rate and select a second signal sampling frequency for the identified heart sound at a second determined heart rate.

14. A system comprising:
a first implantable medical device comprising:
a control circuit;
a sensor, coupled to the control circuit, the sensor configured to sense energy and produce a signal indicative of heart sounds;
a heart sound detector, coupled to the sensor and the control circuit, the heart sound detector adapted to detect heart sounds within the signal indicative of heart sounds;
a parameter circuit, coupled to the control circuit, the parameter circuit configured to store one or more heart sound signal processing parameters, wherein the device acquires and processes heart sound information as a function of the one or more heart sound signal processing parameters;
a triggering circuit, coupled to the control circuit, the triggering circuit configured to transmit a triggering circuit signal to the control circuit upon device detection of a physiologic triggering event, and
wherein the control circuit is configured to:
identify a specified heart sound to sense according to the detected physiologic triggering event; and
change a signal sampling bit resolution based on the identified heart sound.

15. A system comprising:
a first implantable medical device comprising:
a control circuit;
a sensor, coupled to the control circuit, the sensor configured to sense energy and produce a signal indicative of heart sounds;
a heart sound detector, coupled to the sensor and the control circuit, the heart sound detector adapted to detect heart sounds within the signal indicative of heart sounds;
a parameter circuit, coupled to the control circuit, the parameter circuit configured to store one or more heart sound signal processing parameters, wherein the device acquires and processes heart sound information as a function of the one or more heart sound signal processing parameters;
a triggering circuit, coupled to the control circuit, the triggering circuit configured to transmit a triggering circuit signal to the control circuit upon device detection of a physiologic triggering event, and
wherein the control circuit is configured to:
identify a specified heart sound to sense according to the detected physiologic triggering event; and
change a noise blanking interval based on the identified heart sound.

16. A system comprising:
a first implantable medical device comprising:
a control circuit;
a sensor, coupled to the control circuit, the sensor configured to sense energy and produce a signal indicative of heart sounds;
a heart sound detector, coupled to the sensor and the control circuit, the heart sound detector adapted to detect heart sounds within the signal indicative of heart sounds;
a parameter circuit, coupled to the control circuit, the parameter circuit configured to store one or more heart sound signal processing parameters, wherein the device acquires and processes heart sound information as a function of the one or more heart sound signal processing parameters;

a triggering circuit, coupled to the control circuit, the triggering circuit configured to transmit a triggering circuit signal to the control circuit upon device detection of a physiologic triggering event, and wherein the control circuit is configured to:
identify a specified heart sound to sense according to the detected physiologic triggering event; and
change a data acquisition buffer length based on the identified heart sound.

17. A system comprising:
a first implantable medical device comprising:
a control circuit;
a sensor, coupled to the control circuit, the sensor configured to sense energy and produce a signal indicative of heart sounds;
a heart sound detector, coupled to the sensor and the control circuit, the heart sound detector adapted to detect heart sounds within the signal indicative of heart sounds;
a parameter circuit, coupled to the control circuit, the parameter circuit configured to store one or more heart sound signal processing parameters, wherein the device acquires and processes heart sound information as a function of the one or more heart sound signal processing parameters;
a triggering circuit, coupled to the control circuit, the triggering circuit configured to transmit a triggering circuit signal to the control circuit upon device detection of a physiologic triggering event, and wherein the control circuit is configured to:
sample heart beats in response to the detected physiologic triggering event; and
select heart beats for inclusion in a calculated ensemble average according to the detected physiologic triggering event.

* * * * *